(12) United States Patent
Gjerde

(10) Patent No.: US 7,612,165 B2
(45) Date of Patent: Nov. 3, 2009

(54) SOLID-PHASE SYNTHESIS IS A CAPILLARY

(75) Inventor: Douglas T. Gjerde, Saratoga, CA (US)

(73) Assignee: PhyNexus, Inc., San Jose, CA (US)

( * ) Notice: Subject to any disclaimer, the term of this patent is extended or adjusted under 35 U.S.C. 154(b) by 29 days.

(21) Appl. No.: 11/361,128

(22) Filed: Feb. 24, 2006

(65) Prior Publication Data

US 2006/0199945 A1    Sep. 7, 2006

Related U.S. Application Data

(60) Provisional application No. 60/658,553, filed on Mar. 3, 2005.

(51) Int. Cl.
*A61K 38/00*    (2006.01)
*A61K 51/00*    (2006.01)
*C07K 1/00*    (2006.01)

(52) U.S. Cl. .................. 530/333; 530/344; 424/1.69
(58) Field of Classification Search .................. 530/333
See application file for complete search history.

(56) References Cited

U.S. PATENT DOCUMENTS 5,376,252 A * 12/1994 Ekstrom et al. ............. 204/603
6,043,353 A     3/2000 Pon et al.
6,759,126 B1 * 7/2004 Malik et al. ................. 428/391

FOREIGN PATENT DOCUMENTS

WO    WO/03/104814    12/2003

OTHER PUBLICATIONS

Lindsay. http://www.dvdreview.com/fullreviews/supersize_me.shtml; Sep. 28, 2004).*
Lemonick (http://www.time.com/time/2004/cholesterol/drano.html, Nov. 17, 2003).*
A. Baerga-Ortiz, et al., "Epitope Mapping of a Monoclonal Antibody Against Human Thrombin by H/D-Exchange Mass Spectrometry Reveals Selection of a Diverse Sequence in a Highly Conserved Protein," Prot. Sci., 2002 pp. 1300-1308, vol. 11.
M.H. Caruthers et al., "Chemical Synthesis of Deoxyoligonucleotides by the Phosphoramidite Method," Methods in Enzymology, 1987, pp. 287-313, vol. 154.
S.J. Horvath et al., "An Automated DNA Synthesizer Employing Deoxynucleoside 3'- Phosphoramidites," Methods in Enzymology, 1987, pp. 314-326, vol. 154.
A. Vasella, "An Approach to the Synthesis of Polysaccharide Analogues," Pure & Appl. Chem., 1998, pp. 425-430, vol. 70, No. 2.
P. Lloyd-Williams, et al., "Chemical Approaches to the Synthesis of Peptides and Proteins," 1997 by CRC Press LLC, Chapters 1 and 2.

* cited by examiner

*Primary Examiner*—Cecilia Tsang
*Assistant Examiner*—Maury Audet
(74) *Attorney, Agent, or Firm*—Christopher M. Holma; Sue S. Kalman; Cynthia R. Moore

(57) ABSTRACT

The invention provides, inter alia, methods for synthesizing a molecule on the channel surface of a capillary, comprising the steps of: (i) covalently attaching a first chemical entity to the channel surface of a capillary; and (ii) covalently attaching a second chemical entity to the first chemical entity, wherein the covalent attachment steps are part of a process for synthesizing a molecule on the channel surface.

20 Claims, 1 Drawing Sheet

SOLID-PHASE SYNTHESIS IS A CAPILLARY

CROSS REFERENCE TO RELATED APPLICATIONS

This application claims priority to and benefit of U.S. Provisional patent application Ser. 60/658,553 filed Mar. 3, 2005; U.S. patent application Ser. No. 10/434,713, filed May 8, 2003; U.S. patent application Ser. No. 10/733,685, filed Dec. 10, 2003; U.S. patent application Ser. No. 10/733,664, filed Dec. 10, 2003; U.S. patent application Ser. No. 10/733,534 filed Dec. 10. 2003; U.S. patent application Ser. No. 10/792,975 filed Mar. 4, 2004; U.S. patent application Ser. No. 10/793,449 filed Mar. 4, 2004; and U.S. patent application Ser. No. 10/754,775 filed Jan. 8, 2004, the disclosures of which are incorporated herein by reference in their entirety for all purposes.

FIELD OF THE INVENTION

This invention relates to solid-phase synthesis in a capillary. In some embodiments a polymer is synthesized on the internal surface of the capillary. Specific examples of the synthesized polymers would include biopolymers such as polypeptides, polysaccharides and polynucleotides.

BACKGROUND OF THE INVENTION

Solid-phase organic synthesis involves deliberately performing chemical reactions in heterogeneous rather than homogeneous media. The origins of the technology are attributed to Robert Merrifield and Robert Letsinger. Merrifield developed methods of automating the synthesis of peptides on minute, insoluble, chemically-inert polymer beads, for which he won the Nobel Prize in 1984. In parallel findings, Robert Letsinger of Northwestern University developed polynucleotide synthesis on solid phases, which led to the development of the DNA synthesis machines.

The solid phase method has inherent advantages in some synthetic processes, in that undesirable by-products may be removed easily by filtration and yields of reaction may be higher. Other advantages include the immobilization of odiferous and/or environmentally dangerous materials, and the recovery of optically-active materials. Using this basic platform, drug companies are using solid phase organic synthesis in a process called combinatorial chemistry. This process is used to prepare thousands of possible drugs simultaneously for rapid biological screening In spite of the power of modern solid-phase synthesis techniques, there is still much room for improvement. In particular, even the best solid-phase synthesis methods result in some failure sequences, which ultimately limit the ability to synthesize long polymer chains of high purity. It would be desirable to have available a technique which addresses these limitations, allowing for the synthesis of longer chains of higher purity.

It would also be desirable to have solid-phase synthesis techniques that facilitate the preparation of capillaries having polymers attached to the internal surface of the capillary. For example, such capillaries would be useful in a variety of extraction processes that employ extraction capillaries having extraction groups attached to the capillary. In certain applications, it would be advantageous to synthesize the extraction polymer directly on the internal surface of the capillary, i.e., in situ synthesis, rather than the standard technique of synthesizing the polymer and then attaching the fully formed polymer to the capillary.

Accordingly, the need exists for improved methods and reagents for solid phase synthesis and/or methods of performing solid phase synthesis directly on the internal surface of a capillary. The present invention addresses this need by providing new methods and reagents for performing solid-phase synthesis on the internal surface of a capillary column.

DESCRIPTION OF SPECIFIC EMBODIMENTS OF THE INVENTION

Figure 1:
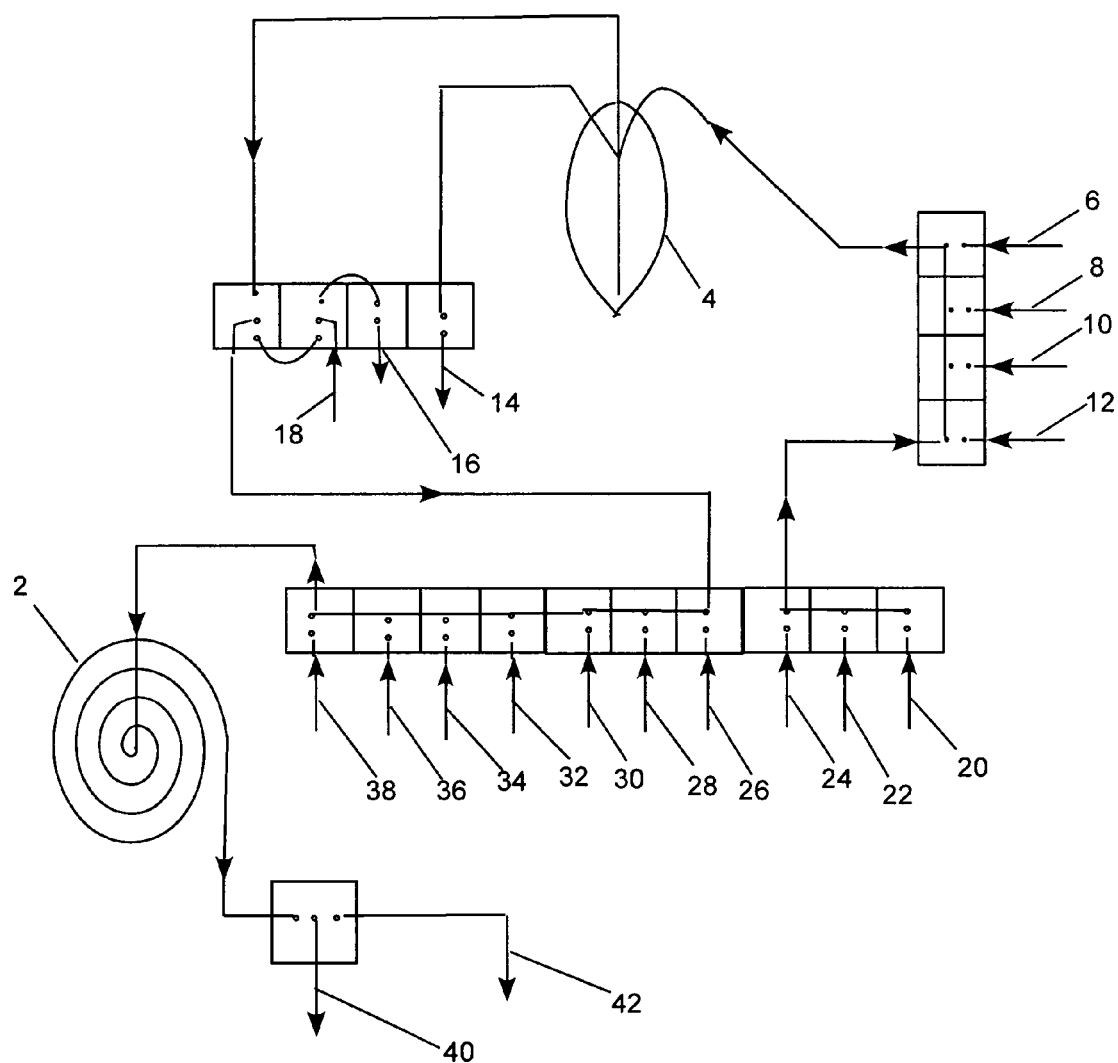
FIG. 1 depicts a capillary-based DNA synthesizer useful for synthesizing a free oligonucleotide.

In accordance with the present invention there may be employed conventional chemistry, biological and analytical techniques within the skill of the art. Such techniques are explained fully in the literature. See, e.g., ION CHROMATOGRAPHY, Gjerde, D. T. and Fritz, J. S. (2000) WILEY-VCH Verlag GmbH; DNA CHROMATOGRAPHY, Gjerde, D. T., Hanna, C. P. and Hornby, D. (2002) WILEY-VCH Verlag GmbH; Antibody Purification Handbook, Amersham Biosciences, Edition AB, 18-1037-46 (2002); Protein Purification Handbook, Amersham Biosciences, Edition AC, 18-1132-29 (2001); Affinity Chromatography Principles and Methods, Amersham Pharmacia Biotech, Edition AC, 18-1022-29 (2001); The Recombinant Protein Handbook, Amersham Pharmacia Biotech, Edition AB, 18-1142-75 (2002); and Protein Purification: Principles, High Resolution Methods, and Applications, Jan-Christen Janson (Editor), Lars G. Ryden (Editor), Wiley, John & Sons, Incorporated (1989); Chromatography, $5^{th}$ edition, PART A: FUNDAMENTALS AND TECHNIQUES, editor: E. Heftmann, Elsevier Science Publishing Company, New York, pp A25 (1992); ADVANCED CHROMATOGRAPHIC AND ELECTROMIGRATION METHODS IN BIOSCIENCES, editor: Z. Deyl, Elsevier Science BV, Amsterdam, The Netherlands, pp 528 (1998); MOLECULAR CLONING, THE CONDENSED PROTOCOLS: A LABORATORY MANUAL, David W. Russell, Joseph Sambrook, Carleen Ann Irwin, and Kaaren A. Janssen, Cold Spring Harbor Laboratory Press, Cold Spring Harbor, N.Y. (2006), DNA MICROARRAYS: A MOLECULAR CLONING MANUAL by David Bowtell (Editor), Joseph Sambrook (Editor), Cold Spring Harbor Laboratory Press, Cold Spring Harbor, N.Y. (2003), CHROMATOGRAPHY TODAY, Colin F. Poole and Salwa K. Poole, and Elsevier Science Publishing Company, New York, pp 394 (1991).

In its various embodiments, the invention employs any of a number of standard techniques and reagents used in conventional organic synthesis. General guidance with respect to these techniques and reagents can be found in any of a variety of texts well known in the art, see for example: F. Dorwald ORGANIC SYNTHESIS ON SOLID PHASE, Wiley VCH Verlag Gmbh, Weinheim 2002; "Organic Chemistry on Solid Supports" by Fruchtel et al., Angew. Chem. Int. Ed. Engl., 1996, 35, pgs. 17-42, "Protecting Groups in Organic Synthesis, Green, T. W. and Wuts, P. G. M. eds, (3d Ed. 1999 ("Greene et al."), (See, e.g., "Solid-Phase Synthesis: A Practical Guide" S. Kates and F. Alberico Eds., (Marcel Dekker, 2000); "Methods in Enzymology, Vol. 289, Solid-Phase Peptide Synthesis" G. B. Fields Ed. (Academic Press, 1997); "Fmoc Solid Phase Peptide Synthesis: A Practical Approach" W. C. Chan (Oxford University Press, 2000); "Protecting Groups in Organic Synthesis, Green, T. W. and Wuts, P. G. M. eds, (3d Ed. 1999), particularly p. 454-649; 2002/3 Novabiochem Catalog; "Synthetic Peptides, A User's Guide," G. A. Grant, Ed., W.H. Freeman & Company, New York, N.Y., 1992; Advanced Chemtech Handbook of Combinatorial & Solid Phase Organic Chemistry (1998); "Principles of Peptide Synthesis, $2^{nd}$ ed.," M. Bodanszky, Ed., Springer-Verlag, 1993; "The Practice of Peptide Synthesis, $2^{nd}$ ed., M. Bodanszky and A. Bodanszky, Eds., Springer-Verlag, 1994; "Protecting Groups," P. J. Kocienski, Ed., Georg Theime Verlag, Stuttgart, Germany, 1994; R. Merrifield, J. Org. Chem. 43:4808-4816 (1978); V. V. Samukov et al., Tetrahedron Lett. 35:7821-7824 (1994); B. W. Bycroft et al., J. Chem. Soc. Chem. Comm. 776-777 (1993); M. Royo et al., Tetrahedron Lett., 33:2391-2394 (1992); and S. C. Miller, J. Am. Chem. Soc. 119:2301-2302 (1997)).

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "a molecule" includes a plurality of such molecules and reference to "the detection method" includes reference to one or more detection methods and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The subject invention pertains to solid phase synthesis on the internal channel of a capillary.

The subject invention involves the solid-phase synthesis of a molecule on the internal surface of a capillary tube. In particular, the molecule can be a biopolymer or heteropolymer such as a polypeptide, polynucleotide, or polysaccharide. The invention is generally applicable to any of a wide variety of capillaries, varying in size, dimensions, and material of construction. Preferably, the internal surface of the capillary should be amenable to chemical derivitization and compatible with the reagents and solvents used in the solid-phase synthesis reaction. In this invention, the internal surface of the capillary functions as the solid support in a solid-phase synthesis reaction, either directly or indirectly. Thus, the terms "solid support," "internal surface of the capillary" and "channel surface" can be used interchangeably herein The composition of the support is not particularly restricted and is within the purview of a person skilled in the art. Thus, for example, the solid support can comprise any of a variety of materials employed in conventional solid-phase synthesis. Thus, the solid support may be an inorganic substance. Non-limiting examples of suitable inorganic substances may be selected from the group consisting of silica, fused silica, porous glass, aluminosilicates, borosilicates, metal oxides (e.g. aluminum oxide, iron oxide, nickel oxide) and clay containing one or more of these. Alternatively, the solid support may be an organic substance such as a cross-linked polymer. Non-limiting examples of a suitable cross-linked polymer may be selected from the group consisting of polyamide, polyether, polystyrene, polycarbonate, fluoropolymer, and mixtures thereof. Preferred supports for use herein include capillaries of fused silica, polystyrene or nylon.

As used herein the term "fused silica" refers to silicon dioxide ($SiO_2$) in its amorphous (glassy) state, which is a species of the broader genera of compositions commonly referred to as high quality synthetic glass of nearly pure $SiO_2$. The term "synthetic fused silica" refers to amorphous silicon dioxide that has been produced through chemical deposition rather than refinement of natural ore. This synthetic material is of much higher purity and quality as compared to fused quartz made from natural minerals. Examples of fused silica capillaries relevant to this invention include those produced by Polymicro Technologies, LLC of Phoenix, Ariz. and SGE Inc. of Ringwood, Australia. In some cases, it is beneficial to etch a fused silica capillary (e.g., by treatment with base) prior to derivatization with an extraction surface, as described in U.S. patent application Ser. No. 10/434,713.

When using silica capillary, it can be useful to assay the number of silanol groups, e.g., before, during or after derivatization with an extraction surface. Methods of assaying for silanol groups are described in co-pending U.S. patent application Ser. No. 10/733,685, filed Dec. 10, 2003, incorporated by reference herein in its entirety.

The term "capillary" is used broadly herein to denote any open channel having opposite open ends (i.e., an inlet and outlet) such that liquid can be passed through the length of the channel, and where the channel has a relatively small cross-sectional area. The term "cross-sectional area" refers to the area of a cross section of the channel, i.e., a planar section of the channel generally perpendicular to the flow of solution through the channel. In preferred embodiments the channel is round (tubular), the cross section is generally circular and the cross sectional area is simply the area of the circle defined by the channel cross section (area=$\pi r^2$). For example, a fused silica capillary having an inner diameter of 204 μm, as can be obtained from Polymicro Inc. (Phoenix, Ariz., lot #PBW04A), has a cross sectional area of $\pi \times (102 \mu m)$=32,685 $\mu m^2$. In preferred embodiments of the invention, the capillary employed has a channel cross-sectional area of less than 7 mm, which corresponds to tubular capillary having an inner diameter of about 3 mm. More preferred are tubular capillaries having smaller internal diameters, e.g., less than about 1 mm, less than about 700 μm, less than about 400 μm, less than about 200 μm, less than about 100 μm, or less than about 50 μm. Thus, some embodiments involve tubular capillaries having internal diameters falling within ranges extending from a lower limit of 5 µm, 10 µm, 20 µm, 30 µm, 40 µm, 50 µm, 70 µm, 100 µm, 150 µm, 200 µm, 300 µm, 400 µm, 500 µm, 600 µm, 700 µm, 800 µm, 900 µm, or 1 mm, to an upper limit of 20 µm, 30 µm, 40 µm, 50 µm, 70 µm, 100 µm, 150 µm, 200 µm, 300 µm, 400 µm, 500 µm, 600 µm, 700 µm, 800 µm, 900 µm, 1 mm, 2 mm or 3 mm. In cases where non-tubular capillaries are used, ranges of cross-sectional areas suitable for use in the present invention are those which are equivalent to the cross-sectional areas of the above-recited tubular capillaries. Non-tubular capillaries suitable for use in the invention could have any of a variety geometries of the channel, e.g., the channel can be square, oval, octoganol, rectangular, or the like.

In some preferred embodiments of the invention, the capillary is an individual stretch of conventional capillary tubing. In other embodiments, the capillary can assume other formats, so long as it includes a channel satisfying the structural and functional criteria set forth herein. Examples include a capillary tube, a bundle of tubes, a solid block or chip having one or more passageways or flow cells running therethrough, e.g., a microfluidics device such as those associated with BiaCore, Inc. (Piscataway, N.J.), Gyros, Inc. (Uppsala, Sweden), Caliper Technologies, Inc. (Mountain View, Calif.) and the like. The passageways can have linear or non-linear central axes, e.g., they can be coiled, curved or straight. The cross-sectional geometry of the passageway is not critical, so long as it allows the channel to function as an extraction channel. For example, capillary tubes having a round cross-sectional geometry work well and can be purchased from a number of vendors. However, other geometries, such as oval, rectangular or another polygonal shape, or a combination of such shapes, can also be employed.

Whatever the geometry of the channel, it is preferred that the dimensions be such that reaction solutions can be passed through the capillary to effect solid-phase synthesis on the internal surface of the capillary, and such that the internal surface has sufficient capacity to synthesize the desired quantity of product.

The inner walls of the channel can be relatively smooth, rough, textured or patterned. Preferably, they are relatively non-porous. The inner surface can have irregular structure such as is described by Paul Kenis, et al., (2000) Acc. Chem. Res., 33:84 and Paul Kenis, et al., (1999) Science, 285:83.

In embodiments of the invention employing silica capillary tubing, the tubing can be beneficially coated with a flexible coating material, typically a polymer or resin. Preferred coating materials include polyimide, silicone, polyacrylate, aluminum or fluoropolymer, especially semiconductor grade polyimide, polystyrene, cyclic olefins (Zeonor®), polymethylmethacrylate, fluoroplastic, and acrylic.

Some embodiments of the invention involve the use of a capillary having a length of greater than 5 cm, especially in the range of 10 cm to 10 m, 20 cm to 2 m, or 100 cm to 1 m. In other cases the range of capillary lengths is shorter, e.g., having a lower limit of 0.1 cm, 0.2 cm, 0.3 cm, 0.4 cm, 0.5 cm, 1 cm, 2 cm, 5 cm or 10 cm, and an upper limit of 1 cm, 2 cm, 5 cm, 10 cm, 100 cm, 1 m or 10 m.

In some embodiments of the invention the channel is coiled into a coil comprising multiple turns, e.g, at least 2 turns, at least 5 turns, at least 10 turns, at least 50 turns, at least 100 turns, or even 200 or more turns. In particular, with respect to fused silica capillary tubing the maximum number of turns is in general limited only by the length of capillary used and the design of the device, as described herein. Thus in some embodiments the number of coils can reach 1000, 2000, 10,000 or even more. Specific teaching regarding the coiling of capillary tubing is provided in the U.S. patent application Ser. No. 10/733,664, filed Dec. 10, 2003, incorporated by reference herein in its entirety.

The structure and configuration of the capillary can assume any of a wide variety of configurations, including but not limited to single and multi-lumen capillaries, such as those available from Paradigm Optics, Inc. (Vancouver, Wash.). The capillary can be provided as a single capillary, or as part of a bundle or array of distinct capillary channels. For example, a bundle of capillary channels can be used in a parallel synthesis procedure. Alternatively, an array of capillaries can be fabricated as a single element, for example, from a fluoropolymer.

In certain embodiments the invention provides methods for performing solid-phase synthesis on the channel surface of a capillary. Examples of the types of molecules that are prepared in this manner include biopolymers, which can be homopolymers or heteropolymers, branched or straight chained. Some specific examples include biological heteropolymers such as peptides, oligonucleotides and oligosaccharides. In certain embodiments the polymer contains a specified sequence of various specific amino acids, nucleic acids or saccharides. The polymer can be built up step by step using the various synthesis routes that are used for building polynucleotides, polypeptides and polysaccharides. After synthesis, the biological heteropolymer may be removed through cleavage or a chemical removal processes. In certain embodiments, removal is performed with a slug of liquid to keep the heteropolymer concentrated. In general, the invention can be used to syntheisize virtually any sequential biopolymer that is amenable to synthesis by conventional solid-phase synthesis techniques. Thus, in one embodiment, the invention can be used for synthesizing a combinatorial library. In general, it has been discovered that internal channel of a capillary can in many instances serve as particularly effective solid-phase support for a solid-phase synthesis reaction. Thus, in general, a known solid-phase synthesis scheme using a conventional solid-phase support, e.g., a resin bead, can be modified using the teaching provided herein, in conjunction with the fundamental principles of chemical synthesis known to one of skill in the art, to arrive at a solid-phase synthesis method of the invention.

In certain embodiments, the invention provides method aimed at synthesizing a molecule of interest on the channel surface of a capillary, and then using the chemically derivatized capillary directly in some process. For example, the covalently bound molecule can be used as an affinity or extraction agent to bind a conjugate molecule. Various methods of performing solid-phase extractions in a capillary are described in US Patent Application Numbers US2004/0126890, US2004/0224329, US2004/0223880, US2004/0224362, and US2004/0241721. In many of the methods described in the afore-mentioned patent applications, the pre-synthesized affinity or extraction reagent is covalently or non-covalently bound to the inner surface of a capillary. For example, in some examples proteins are covalently attached to the surface of a capillary, while in others biotinylated oligonucleotides are non-covalently affixed to streptavidin-coated capillaries. By use of the present invention, the attached affinity reagent can be synthesized directly on the channel surface, i.e., the reagent is synthesized in situ. In situ synthesis can have many advantages compared to post-synthesis attachment, as exemplified by examples provided herewith. As used herein, the term "in situ synthesis" refers to this mode of synthesis where the synthesized molecule is not cleaved from the capillary, but rather is used in its capillary-associated form. In certain embodiments of the invention, a capillary derivatized with an in situ generated peptide can be used in peptide epitope mapping experiments.

In other embodiments of the invention, the synthesized molecule is released from the channel surface and collected, i.e., the objective of the solid-phase synthesis reaction is production of a free molecule, as opposed to a molecule attached to a capillary. For example, the invention can be used as an alternative approach for the synthesis of peptides, oligonucleotides, oligosachharides, peptide-oligonucleotide hybrids, and the like. As used herein, the term "free synthesis" is used to refer to this mode of synthesis, where the synthesized molecule is cleaved from the capillary to produce a free molecule.

While the invention is not intended to be limited by any underlying theories or mechanisms, it is believed that there are a number of advantages to the use of a capillary channel wall as the support for solid-phase synthesis. Prior to this disclosure, these advantages have apparently not been described or generally recognized in the field. For example, one advantage of using a capillary as opposed to a conventional solid-phase synthesis support, e.g., a resin bead, is that the capillary channel surface can provide a less sterically restricted environment for extension of the nascent synthesized molecule. In conventional solid-phase synthesis, the nascent molecule grows on the surface of a bead. Many of the beads used for solid-phase synthesis are porous, and the nexus at which the nascent molecule is attached to the resin is often inside these pores. The walls of the pore can sterically hinder the growth of the molecule and/or the free access of reagents to nascent molecule. This steric hindrance can serve to impede the synthesis, and can pose a particular problem in cases where the molecule being synthesized is large, such as a relatively long peptide or oligonucleotide.

Another source of steric hindrance in conventional solid phase synthesis can arise from the close packing of the solid-support beads. For example, many times in conventional solid phase synthesis, the synthesis occurs in bed of packed beads. The beads are typically packed in a reaction column, or in a reaction vessel, and this inter-bead interaction can sterically hinder synthesis on the bead surface, similar to the intra-bead steric hindrance that can occur inside the pores of certain beads.

Solid-phase synthesis on channel surface of a capillary, on the other hand, is not accompanied by same steric hindrance effects. The nascent molecule is free to grow unencumbered on the channel surface. This can result in fewer failed synthesis steps and more complete reactions than in conventional techniques. For example, in the case of peptide or oligonucleotide synthesis, the result can be fewer failure sequences and the ability to synthesize longer chains with higher yields.

This lack of steric hindrance can facilitate many aspects of the synthesis. Not only does it allow for unencumbered growth of large polymers, it also facilitates each step in the synthesis by allowing clean, rapid introduction of reagents to the site of synthesis, as well as allowing thorough washing of the nascent molecule after each step in the synthesis. Because of these and other factors, the synthesized molecule can be more pure and of a higher quality than comparable molecules synthesized using conventional methodology.

A further advantage of solid-phase synthesis in a capillary is that it can allow for very precise temperature control. In certain chemical synthesis steps, it is desirable to control the temperature of the reaction. This can be accomplished quite precisely and rapidly in a capillary, since the ratio of capillary channel surface area to liquid volume is large. Thus, the temperature of the reaction can be quickly and precisely adjusted by altering the heat of the capillary. This regulation of the temperature of the capillary can be accomplished using any of a variety of methods known in the art, such as by positioning the capillary in an air bath or liquid bath. By regulating the temperature of the bath, it is possible to precisely regulate the temperature of the reaction.

A further advantage of solid-phase synthesis in a capillary is that it allows for the use of very small volumes of reactant solutions. This is due in part to the very low dead volumes of capillary reactors. Conventional solid phase supports can have dead volumes where reactant solutions can be unproductively diverted. In contrast, a very small slug of reactant solution can be passed through a capillary. The smaller the diameter of the capillary, the greater the ratio of surface area to volume, and thus very small volumes of reactant solution can be passed through the capillary while still achieving effective contact between the surface and the solution.

Chemical reactions in the synthesis process can be driven towards completion by increasing the effective time of interaction between reactant solutions and the nascent, solid-support bound molecule. In addition, the ability to wash away reaction products drives the reaction towards completion by mass action effects, resulting in higher effective concentrations of reactants. The effective contact time for a given volume of reactant solution can be increased by increasing the residence time of the solution in the capillary, which can be achieved by slowing the flow of the solution through the column and/or by multiple passages of the solution through the capillary. In US Patent Application Number US2004/0241721, a number of methods are described for controlling the passage of liquid through an extraction capillary, and for achieving multiple passages of a solution through a capillary. These same methods, and straight forward variations thereof, can be used to achieve the same ends in the context of solid-phase synthesis. For example, multiple passages can be achieved by passing liquid back and forth through a capillary multiple times, thereby increasing the residence time of the solution in the capillary. The flow rate of the liquid through the capillary can also be slowed, or even stopped completely for some desired incubation time, in order to increase the residence time of the solution in the capillary.

The volume of the reactant solution can vary, ranging from substantially greater than the volume of the capillary to substantially less than the volume of the capillary. For example, one way to drive a reaction to completion is to use a relatively large volume of reactant solution, and to pump this solution through the capillary at a flow rate and for a length of time that will result in the desired extent of reaction. Alternatively, a smaller volume can be used, such as volume equal to only slightly greater than the volume of the channel, a volume equal to the volume of the channel, or a volume that is only a fraction of the volume of the channel (e.g., less than 90%, 80%, 70%, 60%, 50%, 40%, 30%, 20%, 10%, 5%, 2%, 1%, 0.5%, or 0.1% of the total capillary volume). Solution that is being passed through the capillary is sometimes referred to as a "slug" of liquid. The "slug" designation is particularly appropriate where the volume of liquid is smaller than the volume of the channel, and the slug is being manipulated back and forth through the capillary. In some preferred embodiments, the reactant solution is a solution for cleaving a synthesized molecule off of the capillary and/or for eluting the molecule off the capillary.

The ability to precisely manipulate a slug of liquid through a capillary is one of the features of a capillary that distinguish it from other solid-phase synthesis support materials. Thus, chemical reactions can be achieved in a capillary using a slug of liquid having a very small volume, i.e., only a fraction of the volume of the capillary, where the slug is moved back and forth through the length of the capillary, for a number of passages and at a rate which will allow for the requisite interaction time between the liquid and the reaction surface. It is important that the flow rate of a slug of solution through the capillary is such that the integrity of the slug is not disturbed. A flow rate that is too fast can result in the slug breaking up, which can be undesirable. In some protocols, the flow of the slug is stopped for a period of time and allowed to incubate in the section of the capillary wherein it is positioned.

One important feature of capillaries is that, in many cases, after a slug of liquid has passed through a capillary it will leave a film of liquid upon the capillary channel surface. Thus, a slug that has a volume less than the total capillary volume will only be in direct contact with some fraction of the capillary at any given time. For example, if the volume of the slug is 10% of the total volume of the capillary, it will be in contact with only the 10% of the capillary in which it is positioned. The slug can be moved back and forth, so that over a course of time it is brought into contact with the entire length of the capillary, but at any given time it will only be in contact with 10% of the capillary. However, after it has passed the length of the capillary, it will have left a thin film of reactant liquid upon the length of the capillary surface, wherein the chemical reaction can continue even after the slug has passed on. Thus, the chemical reaction can continue throughout the length of the capillary, not just in the location where the slug is presently residing, i.e., the reaction does not stop at a given location on the capillary surface just because the slug has passed on. Of course, the effective volume of the thin film at any particular location on the capillary surface is much less than the effective volume of a slug of liquid. Thus, as the reaction proceeds the local concentration of reactant in the film can be depleted to an extent that will slow the rate of reaction. Passage of the slug back across that section of the capillary can recharge the film with the depleted reactant, thus serving to drive the reaction to completion by mass action.

Solid-phase synthesis reactions will typically involve the passage of multiple different reactant solutions through the capillary, often in processes involving cycles of reiterated process steps. One of the most critical steps in free synthesis reactions is the cleavage step, where the synthesized molecule is cleaved from the solid support and eluted from the capillary. In some situations it can be beneficial to use a small slug of cleavage solution, for example, to minimize the volume of the eluted sample, which results in a higher concentration of the synthesized molecule. Thus, a slug of cleavage solution having a volume substantially less than the volume of the capillary can be passed back and forth through the capillary, which will create a thin film wherein the reaction can continue even when the slug is residing in a different section of the capillary. After the slug has passed back and forth for a number of times and at a rate sufficient to achieve the desired degree of cleavage, the slug containing the free molecule is released from the capillary.

In using slug cleavage, a product cleavage and elution procedure can be adapted to take advantage of the properties inherent in a slug moving through a capillary, and of the relationship between the composition of the slug and the composition of the film of liquid coating the capillary surface before and after passage of the slug. If the slug is passed back and forth through the capillary multiple times, the slug will approach equilibrium with the film, resulting in similar or substantially the same compositions for slug and film. If the slug makes a single, unidirectional passage through the capillary, the composition of the trailing edge of the film (the film coating the section of the capillary immediately following the position of the moving slug) will be similar or substantially the same as that of the slug. This can result in a film having a concentration profile, i.e., the composition of the film varies along the length of the capillary.

Likewise, the slug itself can have a concentration profile, particularly where the cleavage reaction is occurring at the leading front of the slug and the rate of diffusion of cleavage product through the slug is slow relative to the duration of the cleavage and elution step. In this scenario, a wave front elution can be achieved, where the concentration of product in the slug is higher at the leading edge of the slug. For applications where a particularly high concentration of cleaved product is desired, a user can choose to collect only the leading edge of the slug, rather than the entire slug, thereby obtaining a small volume but highly concentrated sample of the desired product.

Introduction of a reactant solution into the capillary channel, manipulation of the solution within the channel, and the expulsion of the liquid from the channel, can be accomplished by any of a number of techniques for driving or drawing liquid through a channel. Examples would include use of a pump (e.g., a syringe or piston peristaltic, rotary vane, diaphragm, pressurized or vacuum chamber, centrifugal pump, electrokinetic pump, or an induction based fluidics pump), gravity, centrifugal force, capillary action, or gas pressure to move fluid through the capillary. The sample solution is preferably moved through the channel at a flow rate that allows for adequate contact time between the reactant(s) and the solid-phase synthesis surface. The sample solution can be passed through the capillary more than one time, either by circulating the solution through the channel in the same direction two or more times, or by passing the sample back and forth through the channel two or more times (e.g., by oscillating a slug or series of slugs of desorption solution in the channel). In some embodiments it is important that the pump be able to pump air, thus allowing for liquid to be blown out of the channel. Preferred pumps have good precision, good accuracy and minimal hysteresis, can manipulate small volumes, and can be directly or indirectly controlled by a computer or other automated means, such that the pump can be used to aspirate, infuse and/or manipulate a predetermined volume of liquid. The required accuracy and precision of fluid manipulation in the channel will vary depending on the requirements of the particular chemical reaction, the concentration of reactants, the dimensions of the capillary, and similar factors that will be apparent to one of skill in the art. For example, for a capillary with dimensions of 200 µm id and 1 m in length, the internal volume is approximately 33 µL. A liquid slug of 10% of the capillary volume represents a 3.3 µL volume and a 10 cm length. Movement of the slug to within 2% of each end of the capillary means the slug should be within 4 cm of each end.

Thus, for example, in one embodiment an end of a capillary channel is attached to a syringe pump and the other end is positioned in a reactant solution. The syringe plunger is pulled up to draw the solution into and through the channel. The sample can be drawn through the entire length of the channel, and optionally into the chamber of the syringe. The ability to draw liquid into the syringe is particularly relevant when the sample volume exceeds the volume of the channel. Once the entire volume of sample to be processed has been drawn into the channel and/or syringe chamber, and optionally after some incubation period where the sample is allowed to set in the syringe and/or channel, the syringe plunger is pushed down, driving the sample solution back through the channel and out through the same end from which it entered. At this point, the sample has passed through the capillary twice, once in each direction. If desired, for example to increase interaction of reactant with the channel surface, the drawing in and driving out of the sample solution can be one or more time, e.g., four times, which would result in a total of 8 passes of the solution through the channel. This can be accomplished by other means, e.g., through a vacuum or pressure chamber.

In some embodiments of the invention, after a reactant solution has been passed through a capillary, the bulk of the solution is eliminated from the capillary, and in some cases substantially all of the solution is removed. This can be accomplished to some extent by simply pumping the solution out of the capillary. However, in some cases this can result in residual droplets (or segments) of the liquid remaining in the capillary. In some embodiments, it is desirable to remove these liquid segments from the capillary, for example, by continuing the pumping for an extended period. Another method of removing the segments from the capillary is to blow a gas, such as air, nitrogen or argon through the capillary, thereby "blowing out" and bulk liquid that might be present in the capillary. The choice of the particular gas used will depend in some cases upon the nature of the chemical reaction, e.g., in some cases an inert gas such as argon or nitrogen is called for, while in others air will suffice. In some cases, a wash is used between chemical reaction steps to remove residual reactant and by-products from a previous reaction step. Washing and capillary blow out are sometimes used in combination between reaction steps to remove contaminants from the capillary.

In some cases it is desirable to completely remove substantially all liquid from the capillary. In other cases, it is desirable to maintain the surface of the capillary in a wet state. To maintain the capillary in a wet state, care should be taken to avoid an excessive blow-out step; excessive blow-out can dry out the capillary surface, which in some cases is undesirable. The degree of drying that occurs during the blow-out step can be adjusted in a number of ways, e.g., by increasing the flow rate of gas through the capillary, increasing the duration of the blow-out step, increasing the temperature at which blow out is conducted, and the like.

In some embodiments, a reaction solution is passed through at least some substantial portion of the capillary channel at least twice, and in certain embodiments it can be passed through at least four times, at least eight times, at least twelve times, or even more, in order to achieve the desired effect. Multiple passages can be achieved by passing the solution multiple times through the capillary in the same direction, or can be achieved by reversing the flow of solution so that it flows back and forth through the capillary.

In some embodiments of the invention, the substantial portion of the capillary channel through which the multiple-pass solution is passed comprises at least 50% of the channel, or at least 70% of the channel, or at least 80% of the channel, or at least 90% of the channel, or at least 95% of the channel, or at least 99% of the channel, or substantially the entire length of the channel.

While for purposes of illustration much of the foregoing description has focused on the case where solutions enter and leave the capillary through the same opening, other embodiments can also be employed and are encompassed within the scope of the subject invention. For example, in some embodiments one or more of the solutions enter the capillary from one end and exit through the other, as is normally the case with conventional column chromatography.

The sample can be drawn into the channel or pumped through the channel. The sample may be moved back and forth in the channel as many times as is necessary to achieve the desired desorption. Small particulates and air bubbles typically have little or no effect on performance, but if they become a problem they can be minimized using techniques known in the art.

In some embodiments of the invention, it is desirable to start with a capillary including a functional group in an activated form, e.g., an activated carboxyl. This activation facilitates the first coupling step in the synthesis, e.g., via formation of an amide bond. For example, an activated carboxyl group can take any of a number of forms, including but not limited to activated reactive esters, hydrazides, thiols or reactive disulfide-containing derivatives. A reactive ester can be prepared in any of a number of ways known to those of skill in the art, including by reaction with a carbodiimide. In one embodiment the activated functional group is a 2-aminoethanethiol derivative. In yet another embodiment the activated functional group is a vinyl sulfone. A variety of suitable coupling chemistries are described in US Patent Applications Number US2004/0224329.

In some embodiments, solid phase synthesis occurs directly on the channel surface of the capillary, i.e., the synthesized molecule is attached to the capillary wall, optionally through a linker, handle, or the like. In other embodiments, it occurs in a 3-dimensional matrix that is attached to the capillary surface, either covalently or non-covalently. US Patent Application Number US2004/0224329 describes methods for preparing extraction capillary channels having 3-dimensional extraction surfaces, e.g., a polydextran matrix. These methods can be adapted to prepare a capillary channel coated with a 3-dimensional matrix, wherein the 3-dimensional matrix serves as the solid support for a solid-phase synthesis reaction of the instant invention. For example, the 3-dimensional surface can be prepared by attaching a polymer (e.g., polydextran having an activated functional group for coupling) to a capillary channel. The attachment can be accomplished by means of an interaction between complementary attachment groups on the polymer and channel surface. The term "complementary" refers to the ability of the attachment groups to interact with one another in such a way as to result in attachment of the polymer to the channel. Examples of such interactions include electrostatic attraction (e.g., where the attachment groups are oppositely charged ionic moieties) and hydrophobic interactions (e.g., where the attachment groups are non-polar groups that are attracted to one another, particularly in a polar environment). The interaction can be one that results in the formation of a covalent bond, e.g., the complementary attachment groups are functional groups capable of forming covalent bonds, e.g., a carboxyl group and an amide group are complementary functional groups capable of reacting to form an amide bond, vinyl and thiol are complementary functional groups capable of reacting to form a thioether bond. Other examples of complementary groups are cyanogen bromide and the amine group, which can react to form an isourea bond (Porath et al. (1973) J. Chromatograph. 86:53; and Kohn and Wilchek (1984) Appl. Biochem. Biotechnol. 9:285-304), and maleimide and thiol, which can react to form a thioether bond (Wang et al. (2003) Bioorganic and Medicinal Chemistry 11:159-6; Toyokuni et al. (2003) Bioconjugate Chem. 14:1253-59; Frisch et al. (1996) Bioconjugate Chem. 7:180-86). The maleimide reaction is particularly useful in certain embodiments of the invention for attaching a group to a polydextran matrix with minimal crosslinking of the matrix. The maleimide group is relatively specific for the thiol group, and not prone to unintended reaction with the dextran matrix. Use of the maleimide group as a linker is exemplified further in the examples, where preparation of a polymaleimide dextran is described. This polymaleimide dextran can be a particularly low-crosslinked matrix, which can result in less steric hindrance to the synthesis of larger molecules, as described elsewhere herein.

The attachment of a polymer matrix to a capillary channel can be direct, but more typically is accomplished by one or more linker molecules that serve as intermediaries bridging the polymer and the surface of the extraction channel. Attachments between polymer and linker, linker and channel surface, and/or linker to linker can be covalent or non-covalent. The linker molecule can itself be a polymer, or not. For example, the linker molecule can be a polymer that interacts with the capillary channel and with the extraction polymer, bridging the two. When the capillary channel is silica, for example, surface of the channel is normally covered with silanol groups, resulting in a net negative charge to the surface. A bridge molecule having a positive charge (e.g., a polymer, such as a strong base anion exchanger) can be used to coat the surface, attached thereto by electrostatic attraction.

When employing a silica capillary, it is often convenient to covalently couple the matrix to the capillary through free silanol groups on the channel surface. This is typically accomplished through a linking molecule bridging the silanol group and matrix backbone, e.g., a polymer. For example, reactive thiol or amino groups can be attached via reaction with a thiosilane or aminosilane, respectively. A carboxyl group can be introduced on the capillary surface by reaction of amino-functionalized capillary with an anhydride, e.g., succinic anhydride.

An advantage of the 3-D support surfaces of the subject invention is their high surface area relative to a corresponding 2-D extraction surface (i.e., monolayer), which can allow for improved synthesis capacity. On the other hand, the 3-D matrix might result in steric hindrance effects similar to that experienced with conventional solid-phase synthesis beads, which are avoided by performing the synthesis directly on the 2-dimensional surface of the capillary. These competing factors must be taken into account when designing a synthesis protocol, and will affect the choice of 3-dimensional or 2-dimensional support surfaces.

In some embodiments of the invention, a plurality of solid-phase synthesis reactions are conducted in parallel, e.g., in a multiplex fashion. The use of capillaries facilitates multiplexed reactions, since the capillaries typically have a relatively small diameter, and hence multiple reactions can be run simultaneously in a relatively small space. For example, standard tubular capillaries can be arranged in parallel, such as by bundling them together in a configuration such that fluid can be passed through the channels concurrently. Alternatively, a composite array of capillaries can be employed. When a pump is used to manipulate fluids through the channels, each capillary in the multiplex array can have its own pump, e.g., syringe pumps activated by a common actuator. Alternatively, capillaries can be connected to a common pump, a common vacuum device, or the like. In another example of a multiplex arrangement, the plurality of capillaries is arranged in a manner such that they can be centrifuged, with fluid being driven through the capillaries by centrifugal force.

In one embodiment, synthesized molecules can be arrayed from a synthesis capillary to a plurality of predetermined locations, for example locations on a chip or microwells in a multi-well plate. A precise liquid processing system can be used to dispense the desired volume of eluant at each location. For example, a synthesis capillary containing bound synthesis product can be cleaved with an elution solution, and small aliquots of the elution solution (e.g., 1 µL drops) spotted into microwells using a robotic system such as those commercially available from Zymark (e.g., the SciClone sample handler), Tecan (e.g., the Genesis NPS or Te-MO) or Cartesian Dispensing (e.g., the Honeybee benchtop system). This can be used for high-throughput assays, screening, etc. Many of the methods and apparatus for performing multiplexed capillary extractions, such as are described in U.S. Patent Application US2004/0241721, can be adapted for use in multiplexed synthesis procedures.

The above-described synthesis process can be automated, for example by using software to program a computer controller to control the pumping, e.g., the volumes, flow rates, delays, and number of cycles.

Note that in many cases it is desirable to use more than one pumping system to implement the methods of the invention, e.g., a larger syringe for chemical synthesis reactants and wash solution, and smaller, more precise 50 µL syringe for the cleavage elution step. The reason for this is because the pumping requirements often vary for the elution step as opposed to the synthesis and washing steps.

The position of the slug itself in the capillary can be monitored directly, as described in more detail below. For example, the passage of the slug through a particular point in the capillary can be readily detected by visual or optical means, as the interface between air and liquid is typically quite distinct.

The feedback mechanism for controlling the pump can be used in conjunction with a two pump system as described above, or with a single pump system.

In some embodiments, the invention provides a multiplexed synthesis system comprising a plurality of synthesis channels of the invention, e.g., fused silica capillaries. The system can include a pump or pump in operative engagement with the capillaries, useful for pumping fluid through the capillaries in a multiplex fashion, i.e., concurrently. In some embodiments, each capillary is addressable. The term "addressable" refers to the ability of the fluid manipulation mechanism, e.g., the pumps, to individually address each capillary. An addressable channel is one in which the flow of fluid through the channel can be controlled independently from the flow through any other channel which may be operated in parallel. In practice, this means that the pumping device in at least one of the reactions steps is in contact and control of each individual channel independent of all the other channels. For example, when syringe pumps are used, i.e., pumps capable of manipulating fluid within the capillary by the application of positive or negative pressure, then separate syringes are used at each capillary, as opposed to a single vacuum attached to multiple syringes. Because the capillaries are addressable, a controlled amount of liquid can be accurately manipulated in each capillary. In a non-addressable system, such as where a single pump is applied to multiple capillaries, the liquid handling can be less precise. For example, if the back pressure differs between multiplexed capillaries, then the amount of liquid entering each capillary and/or the flow rate can vary substantially in a non-addressable system. Various embodiments of the invention can also include samples racks, instrumentation for controlling fluid flow, e.g., for pump control, etc. The controller can be manually operated or operated by means of a computer. The computerized control is typically driven by the appropriate software, which can be programmable, e.g., by means of user-defined scripts.

The invention also provides software for implementing the methods of the invention. For example, the software can be programmed to control manipulation of solutions and addressing of capillaries into collection vials, for spotting or introduction into some analytical device for further processing.

The invention also includes kits comprising one or more reagents and/or articles for use in a process relating to solid-phase synthesis, e.g., reagents, chemical linkers, washes, etc.

In general, the invention provides methods for synthesizing a molecule on the channel surface of a capillary, comprising the steps of: (i) covalently attaching a first chemical entity to the channel surface of a capillary; and (ii) covalently attaching a second chemical entity to the first chemical entity, wherein the covalent attachment steps are part of a process for synthesizing a molecule on the channel surface. In some embodiments, the process is repeated iteratively, with the attachment of a third chemical entity, optionally a fourth chemical entity, and so on, such that the total number of chemical entities attached is at least 3, at least 4, at least 5, at least 10, at least 20, at least 30, at least 40, at least 50, at least 60, at least 70, at least 80, at least 90, at least 100, at least 120, at least 150, at least 200, at least 250, at least 300, at least 400, at least 500, at least 600, at least 700, at least 800, at least 900, at least 1000, at least 1500, at least 2000, at least 3000, or greater. The maximum number of chemical entities that can be added will vary depending upon the specific synthesis procedure and the nature of the reactions and reactants, but will generally be greater than can be achieved with an analogous synthesis by conventional means. Thus, in certain embodiments the maximum number of chemical entities that can be added is at least 4, at least 5, at least 10, at least 20, at least 30, at least 40, at least 50, at least 60, at least 70, at least 80, at least 90, at least 100, at least 120, at least 150, at least 200, at least 250, at least 300, at least 400, at least 500, at least 600, at least 700, at least 800, at least 900, at least 1000, at least 1500, at least 2000, at least 3000, least 4000, at least 5000, at least 6000, at least 7000, at least 8000, at least 9000, or greater.

The invention further provides the derivatized capillaries produced by the methods described herein, which have various advantages in methods employing these capillaries, as well as various methods of using the derivatized capillaries.

In certain preferred embodiments of the invention, the molecule synthesized on the channel surface is a polymer or biopolymer, e.g., a heteropolymer or homopolymer, such as a peptide, oligonucleotide or oligosaccharide. As used herein, the term "biopolymer" refers to biological, macromolecular polymers, such as polynucleotides, polypeptides, polysaccharides, and the like, as well as synthetically-generated variants of these naturally occurring molecules, such as peptide nucleic acids and the like. In such embodiments, the chemical entities are typically monomer building blocks that make up the polymer, typically in a blocked form, such at Fmoc or Boc protected amino acids. For example, if the polymer is a peptide, the chemical entities are generally blocked amino acids, if the polymer is a polynucleotide, the chemical entities are blocked nucleosides, etc. As used herein, unless otherwise indicated, the term "amino acid" refers to both blocked and free amino acids, and the term "nucleoside" refers to both blocked and free amino acids.

The first and second chemical entities (as well as the third, fourth, fifth, etc, if used) can be the same or different from one another. For example, in the synthesis of a homopolymer, the chemical entities are typically the same as one another. An example would be the synthesis of a poly-dT oligonucleotide, useful for the capture of polyA-messenger RNA, for which the chemical entities would be appropriately blocked thymidine nucleotides. Alternatively, in the synthesis of a heteropolymer (such as a typical peptide, oligonucleotide or hybrid), the chemical entities can be different from one another, e.g., different, appropriately blocked amino acids or nucleosides, as dictated by the desired sequence to be synthesized.

In some cases, the chemical entities can include linker groups, handles, and the like, for attaching the synthesized molecule to the capillary channel surface, e.g., a linker comprising a cleavable handle. Examples of cleavable linkers include 4-alkylbenzyl alcohol, 4-(hydroxymethyl)phenylacetamide (PAM linker), 4-alkoxybenzyl alcohol (Wang linker), 4-alkoxy-2-methoxybenzyl alcohol and 4-alkoxy-2, 6-dimethoxybenzyl alcohol (HAL linker). Other cleavable and non-cleavable linkers are known in the art and can serve as chemical entities, see for example Chemical Approaches to the Synthesis of Peptides and Proteins, P. Lloyd-Williams, F Alberico, and E. Giralt (1997, CRC Press).

A cleavable linker can be used for a variety of purposes, for example, to free polymer product from solid-support at termination of solid-phase synthesis, or to monitor progress of the reaction prior to completion, e.g., via mass spectrometry. Monitoring via ESI-MS can be accomplished using, for example, a TFA-cleavable linker. When MALDI is the mass spectrometric method used, a photo-cleavable linker may preferably be used.

The capillary surface can be modified to include a functional group for covalent attachment of chemical entities thereto, e.g., amino-functionalized, carboxylic acid-functionalized, thiol-functionalized. Examples of some functionalization protocols are included in the Examples of this specification.

The attachment of chemical entities to the capillary surface can in some cases involve attachment to a 3-dimensional matrix affixed to the capillary surface, as discussed elsewhere herein. 3-dimensional polymeric matrices of the invention can vary substantially in thickness depending upon the dimensions and structure of the capillary and the nature of the synthesis reaction. The three-dimensional surface layer typically has a thickness of from a few angstroms to thousands of angstroms. In some embodiments the surface is between 5 to 10,000 angstroms thick, e.g., 5 to 1000 angstroms. The thickness of the surface can be adjusted as desired based on factors including the dimensions of the capillary channel, the nature of the analyte or analytes of interest, the nature of an affinity group or extraction reagent present in the surface, the desired binding capacity.

In some embodiments of the invention the 3-D solid phase extraction surface is a hydrogel formed from a polymer, e.g., a polysaccharide or a swellable organic polymer. The polymer should be compatible with the analyte of interest and with a minimal tendency towards nonspecific interactions. Examples of suitable polysaccharides include agarose, sepharose, dextran, carrageenan, alginic acid, starch, cellulose, or derivatives of these such as, e.g., carboxymethyl derivatives. Polysaccharides of the dextran type which are non-crystalline in character, in contrast to e.g., cellulose, are particularly suited for use in the subject invention. Examples of water-swellable organic polymer would include polyvinyl alcohol, polyacrylic acid, acrylate, polyacrylamide, polyethylene glycol, functionalized styrenes, such as amino styrene, and polyamino acids. Exemplary polyamino acids include both poly-D-amino acids and poly-L-amino acids, such as polylysine, polyglutamic acid, polyaspartic acid, co-polymers of lysine and glutamic or aspartic acid, co-polymers of lysine with alanine, tyrosine, phenylalanine, serine, tryptophan, and/or proline. A 3-dimensional matrix of the invention should be composed of a material that is compatible with the chemistry reactions of the synthesis.

In certain embodiments of the invention, the synthesized molecule is a peptide. In such cases, standard solid-phase peptide synthesis (SPPS) techniques can be employed, adapted to capillaries as described herein. For example, Fmoc and Boc protection schemes can be used. A variety of support materials can be employed. For example, methods of peptide synthesis on controlled pore glass (CPG) can be adapted for synthesis on a silica capillary surface. See, e.g., Albericio, F.; Kneib-Cordonier, N.; Biancalana, S.; Gera, L.; Masada, R. I.; Hudson, D.; Barany, G. (1990) J. Org. Chem. 55:3730.

General approaches to peptide and protein synthesis, such as those described Chemical Approaches to the Synthesis of Peptides and Proteins, P. Lloyd-Williams, F Alberico, and E. Giralt (1997, CRC Press), can be adapted to the present invention. Some specific examples of peptide synthesis protocols employing the Fmoc/tBu methodology are provided in the Examples section of this specification. The peptide can be cleaved from the capillary, or can be left attached to the capillary and used in a process involving a peptide-derivatized capillary. In order to retain the peptide on the capillary surface, one should use a linker that is stable to the conditions used for the final de-blocking of the peptide, e.g., the deblocking of amino acid functional groups by treatment with TFA. This can be accomplished, for example, by coupling the first amino acid in the chain directly to an amino-functionalized capillary through a peptide bond.

In certain embodiments of the invention, the synthesized molecule is an oligonucleotide or polynucleotide (as used herein, the term "oligonucleotide" is not intended to necessarily denote an upper limit in length, and hence would encompass a polynucleotide). As was the case with peptides, standard solid-phase oligonucleotide synthesis techniques can be adapted to a capillary using the teaching provided herein. The oligonucleotide can be cleaved and eluted from the capillary, or deprotected on the capillary and used while still covalently attached to the capillary. Of course, an appropriate linker should be selected based upon whether the intent is that the oligonucleotide be released or retained on the capillary during the final de-blocking step. Examples of linkers suitable for use in conjunction with this invention can be found throughout the literature. See, for example, Azhayev, A. (1999) Tetrahedron 55:787-800; Pon, R. T. and Yu, S. (1997) Tetrahedron Letters 38(19): 3331-3334; Walsh, A. j., Clark, G. C., and Fraser, W. (1997) Tetrahedron Letters 38(9): 1651-54; Yoo, D. J. and Greenberg, M. M., J. Org. Chem. (1995) 60:3358-64; Bergmann, F. and Bannwarth, W. (1995) 36(11):1832-42; Gao, H., aGaffney, B. L. and Jones, R. A. (1991) 32(40):5477-80; Pon, R. T., Yu, S., and Sanghvi, Y. S. (1999) Bioconjugate Chem. 10:1051-57; Nelson, P. S., Muthini, S., Vierra, M., Acosta, L. and Smith, T. H. (1997) BioTechniques 22:752-56; Pon, R. T. and Yu, S. (1999) Synlett 11:1778-80; and U.S. Pat. Nos. 6,015,895 and 6,043,353.

All publications and patent applications mentioned in this specification are herein incorporated by reference to the same extent as if each individual publication or patent application was specifically and individually indicated to be incorporated by reference.

Having now generally described the invention, the same will be more readily understood through reference to the following examples, which are provided by way of illustration, and are not intended to be limiting of the present invention, unless so specified.

EXAMPLES

The following preparations and examples are given to enable those skilled in the art to more clearly understand and practice the present invention. They should not be construed as limiting the scope of the invention, but merely as being illustrative and representative thereof.

Example 1

Hydroxide Etch-Conditioning of Fused Silica Capillary Tubing

Fused silica capillaries (204 um ID, 362 um OD; 50 meters ×2; obtained from Polymicro Inc. (Phoenix, Ariz., lot #PBW04A) were etched by treatment of the channel surface with 100 mM NaOH for 50 minutes. The capillaries were then washed with water (6.0 mL), 0.1N HCl (2 mL), water (10 mL) and acetonitrile (6 mL), after which they were dried with nitrogen gas.

Example 2

Synthesis of Amino-Functionalized Capillary

A 10 meter section of the etched capillary described in Example 1 was filled with a solution of $(MeO)_3Si(CH_2)_3NH_2$ (400 uL) in toluene (1200 uL). The capillary was placed in a 120° C. oil-bath and the reaction continued for 16 h with the flow of the silanization solution through the capillary adjusted to 0.8 uL/min. The capillary was then washed with toluene (1000 uL), acetonitrile (2000 uL), and dried with nitrogen.

Example 3

Synthesis of Carboxylic Acid-Functionalized Capillary

A four meter length of the amino-functionalized capillary described in Example 2 was filled with a solution of succinic anhydride (125 mg; 1.25 mmol), DMAP (20 mg), pyridine (25 uL) in DMF (400 uL) and acetonitrile (900 uL). The capillary was placed in a 65 C oven and the reaction continued for 15 h with the flow of the succinic anhydride solution adjusted to 0.6 uL/min. The capillary was then washed with acetonitrile (2000 uL).

Example 4

Synthesis of a Peptide Stably Attached to a Capillary Channel Surface

An amino-functionalized fused silica capillary is prepared as described in Example 2. The peptide is synthesized using Fmoc/tBu methodology. Thus, the term Fmoc/tBu-protected, as used herein, refers to an amino acid having an Fmoc-protected α-amino group, and any other reactive functional groups in the amino acid protected by a tBu-type protecting group, i.e, a protecting group that is stable to treatment with 20% piperdine in DMF, but can be removed by treatment with TFA.

The desired first amino acid in the chain (i.e., the C-terminal amino acid in the peptide to be synthesized) is attached to the capillary by passing the Fmoc/tBu-protected amino acid in DMF through the capillary in the presence of the coupling agent HBTU. The Fmoc group is then removed by passing 20% piperdine/DMF through the capillary. The next Fmoc/tBu-protected amino acid, in DMF, is then passed through the capillary, followed once again by deprotection by passage of 20% piperdine/DMF through the capillary. This process of cyclical coupling and deprotection is continued until all the amino acids of the desired peptide have been introduced into the growing chain. Then TFA is passed through the column to remove the groups protecting the functional groups of the amino acid residues, leaving the deprotected peptide attached to the surface.

Example 5

Vinylsulfonedextran Synthesis

Dextran (Fluka, St. Louis, Mo. #31387; MW. 15000-20000; 2 g; 37 mmol of —OH) was dissolved in water (60 mL) and phosphate buffer (pH 11.5; 400 mM $Na_2HPO_4$/NaOH; 20 mL) before $NaBH_4$ (40 mg) was added, followed by divinylsulfone (5.5 mL; 74 mmol; 1.5 eq.; added all at once). The reaction continued at RT for 27 minutes, then quenched by adjusting the pH to 6 with 6N HCl. The light yellow reaction mixture was dialyzed and lyophilized.

Example 6

Synthesis of Thiol-Functionalized Capillary

Etched capillaries were prepared as described in Example 1 and were filled with a solution of $(MeO)_3Si(CH_2)_3SH$ (20% in toluene) before being placed in an oven at ~125° C. The reaction continued for 16 h with the flow of the silanization solution through the capillary adjusted to 0.15 mL/h. The capillaries were washed with toluene (3000 uL), acetonitrile (2000 uL), water (4 mL), acetonitrile (3000 uL), and dried with nitrogen.

Example 7

Synthesis of a Peptide Stably Attached to a Dextran-Coated Channel Surface

Vinylsulfone-dextran (Example 5; 200 mg (dialyzed and freeze-dried)) is dissolved in a solution of 50 mM phosphate buffer (pH=8.5; 3 mL) and DMF (3 mL) is added to clarified the solution. Thiol-functionalized capillaries (Example 6; ~50 meters ×2) are filled with the solution and the reaction is allowed to proceed for 1 h at a flow rate through the capillary of 0.5 mL/h, resulting in a vinylsulfone-dextran-derivatized capillary. Amino functional groups are attached to the dextran by passing a solution of $HSCH_2NH_2$ (200 mM in phosphate buffer at pH 8.0) through the capillary. The desired first amino acid in the chain (i.e., the C-terminal amino acid in the peptide to be synthesized) is attached to the capillary by passing the Fmoc/tBu-protected amino acid in DMF through the capillary in the presence of the coupling agent HBTU. Continued cycles of coupling are then conducted as described in Example 4, followed by deprotection with TFA to generate the peptide-derivatized dextran-coated capillary.

Example 8

Synthesis of a Peptide Stably Attached to a PEG-Coated Channel Surface

A 150 μm ID 75 cm length capillary is etched according to Example 1. The capillary is then filled with a 65° C. 4% (v/v) solution of 3-aminopropyltriethoxy-silane in methanol and reacted for hours with a slow flow of 2 μL/min. After flushing with 100% methanol and then deionized water, the tube is filled with N-hydroxysuccinimido-polyethylene glycol (NHS-PEG) in 50 mM sodium bicarbonate solution at pH 8.3 and reacted for 4 hours at room temperature. Amino functional groups are attached to the dextran by passing a solution of $HSCH_2NH_2$ through the capillary. The desired first amino acid in the chain (i.e., the C-terminal amino acid in the peptide to be synthesized) is attached to the capillary by passing the Fmoc/tBu-protected amino acid in DMF through the capillary in the presence of the coupling agent HBTU. Continued cycles of coupling are then conducted as described in Example 4, followed by deprotection with TFA to generate the peptide-derivatized dextran-coated capillary.

Example 9

Synthesis and Release of a Deprotected Peptide from a Capillary Channel Surface

An amino-functionalized fused silica capillary is prepared as described in Example 2. The peptide is synthesized using Fmoc/tBu methodology. Thus, the term Fmoc/tBu-protected, as used herein, refers to an amino acid having an Fmoc-protected α-amino group, and any other reactive functional groups in the amino acid protected by a tBu-type protecting group, i.e, a protecting group that is stable to treatment with 20% piperdine in DMF, but can be removed by treatment with TFA.

A 4-hydroxymethylphenoxyacetic acid (HMPA) linker is attached to the amino functionalized capillary. (Alternatively, 4-hydroxymethyl benzoic acid (HMBA) can be used as the linker to generate peptides with various C-terminal carboxy modifications, or as an alternative method for synthesizing a peptide-derivatived capillary. HMBA is stable to the TFA deprotection step, but can be cleaved by treatment with a base.) The capillary is washed, and then the desired first amino acid in the chain (i.e., the C-terminal amino acid in the peptide to be synthesized) is attached to the capillary by passing the Fmoc/tBu-protected amino acid in DMF through the capillary in the presence of the coupling agent HBTU. The Fmoc group is then removed by passing 20% piperdine/DMF through the capillary. The next Fmoc/tBu-protected amino acid, in DMF, is then passed through the capillary, followed once again by deprotection by passage of 20% piperdine/DMF through the capillary. This process of cyclical coupling and deprotection is continued until all the amino acids of the desired peptide have been introduced into the growing chain. Then TFA is passed through the column to remove the groups protecting the functional groups of the amino acid residues, at the same time releasing the free peptide, which can then be lyophilized. Optionally, the peptide can be further purified, for example, by reverse-phase chromatography.

Example 10

Synthesis of an Oligonucleotide on a Capillary Channel Surface

In this example, a capillary-based DNA synthesizer is used to synthesize a free oligonucleotide. The general design of the DNA synthesizer is shown in schematic diagram of FIG. 1. The primary reactor is a capillary 2, and the reagent and solvent deliveries are controlled by a series of low-dead volume valves, e.g., the pneumatically actuated diaphragm valves described by Horvath et al. (Meth. in Enzymology (1987) 154:314-326). To move reagents and solvents from the reservoirs, positive argon pressure can be used. The valves are automatically operated by a control unit. A separate reactor, the activation vessel, is designed for the activation of each phosphoramidite prior to coupling. If mixed probes are being synthesized, the activation vessel is also used for the accurate premixing and the simultaneous activation of two, three, or four different phosphoramidites.

The capillary is an amino-functionalized fused silica capillary prepared as described in Example 2.

The activation vessel 4 is a conical Pyrex flask fitted with Teflon tubing connectors. All reagents and solvents are stored in Pyrex bottles (reservoirs) protected from light. All tubing and bottle cap surfaces exposed to chemical vapors or liquid are made of Teflon. Well-controlled argon pressure in each reservoir provides a simple, accurtate and reliable method of reagent delivery that allows for complete purging of previously delivered reagent from the reation train prior to delivery of the next reagent.

Tubings 6-12 are attached to reservoirs containing the appropriate phosphoramidite in solution with acetonitrile. A vent is attached to tubing 14, and tubing 16 is directed to a vent. Tubings 18 and 20 are attached to a supply of argon for controlled movement of solvents and reagents through the system.

Reservoirs containing acetonitrile and tetrazole are attached to tubings 22 and 24, respectively, for use in the activation of the phosphoramidite precursors. Reservoirs containing acetonitrile, dichloromethane, iodine ($I_2/H_2O$:2, 6-lutidine:tetrahydrofuran solution) and tricloroacetic acid are attached to tubings 26, 28, 30 and 32, respectively, for use in oxidation, detrytilation reactions and for washing the capillary. Reservoirs containing thiophenol:triethylammonium:dioxane solution, methanol, and concentrated ammonium hydroxide are attached to tubings 34, 36 and 38, respectively, for use in deprotection and cleavage from the capillary. Tubing 40 goes to a waste used for trityl collection, and tubing 42 to waste from coupling step.

Phosphoramidites

The nucleotide precursors used in the coupling step are the 5-' and base-protected deoxynucleoside 3'-N,N-diisopropylaminophosporamidites: N-6-benzoyl-deoxyadenosine phosphoramidite, N-4-benzoyl-deoxycytidine phophoramidite, N-2-isobutryl deoxyguanosine phosphoramidite, and deoxythymidine phosphoramidite. All of the 5'-hydroxyl groups for all four bases are blocked with a dimethoxytrityl (DMT) group, and all phosphorous linkages are blocked with a cyanoethyl group.

Attachment of First Deoxynucleoside to Capillary Wall

The appropriate base-protected 5'-O-dimethoxytrityl (DMT) deoxynucleoside is reacted with succinic anhydride. After an aqueous extraction against citric acid, the 3'-succinylated deoxynucleoside is converted to the p-nitrophenylester using p-nitrophenol and dicyclohexylcarbodiimide (DCC). This deoxynucleoside is then passed through an amino-functionalized capillary in a mixture of dimethylformamide, dioxane and triethylamine. An intense yellow color forms rapidly, indicating the elimination of p-nitrophenol and the attachment of the deoxynucleoside to the capillary wall. Unreacted amino groups are then acetylated (capped) using standard procedure (Atkinson, T.; Smith, M. In Oligonucleotide Synthesis—A Practical Approach; Gait, M. J. Ed.; IRL Press: Oxford, 1984, pp. 35-81). The capillary 2 is then attached in-line to the DNA synthesizer as depicted in FIG. 1.

De-blocking

The first base attached to the solid support is initially inactive because all of the active sites have been blocked or protected. Prior to adding the next base, the DMT group protecting the 5'hydroxyl group must be removed. This is done by passing 3% trichloroacetic acid (TCA)/dichloromethane (DCM) solution through the capillary. The dimethoxy cations released give a bright orange color in solution with $\lambda_{max}$ 498 nm, and they can be used to quantitativelt monitor the coupling yield of each cycle in the synthesis. Following detritylation, the capillary is flushed with argon, and then washed with dichloromethane to remove any excess reagent or by-products.

Coupling

Following the de-blocking step and wash, the capillary is flushed with argon and then washed with anhydrous acetonitrile. While the capillary is being washed, the selected deoxynucleoside 3'-phosphoramidite:acetonitrile solution (6-12) is delivered to the activation vessel and mixed with 1H-tetrazole:acetonitrile solution 24. The activation is extremely rapid. In mixed base positions, the proper deoxynucleoside 3'-phosphoramidite solutions are delivered into the activation vessel one after the other in a well defined molar ratio and then mixed with the 1H-tetrazole solution. By applying positive argon pressure in the activation vessel and by opening the proper valves, the activated deoxynucleoside 3'-phophoramidite solution passes through the capillary at a flow rate and for a duration sufficient to achieve near quantitative coupling. Subsequent to the coupling, the capillary is flushed with argon and both the activation vessel and the capillary are washed with acetonitrile. The acetonitrile is removed from the activation vessel and purged from the capillary with argon.

Oxidation

The 3'-5' phosphate trimester bond formed in the previous coupling step is oxidized to phosphate triester by using $I_2$ in a water:2,6-lutidine:tetrahydrofuran solution. Following oxidation, the capillary is flushed with argon, then washed with acetonitrile, and then flushed with argon again. $I_2$ is then removed from the capillary by washing it with acetonitrile.

This cycle of activation, de-blocking, coupling and oxidation is repeated until all desired based have been added to the oligonucleotide.

Deprotection and Cleavage from Capillary

Once the synthesis cycle described above is repeated the desired number of times, the bound, protected oligonucleotide is freed of protecting groups and cleaved from the silica support. The deprotection procedure starts by passing a thiophenol:triethylammonium:dioxane solution from tubing 34 through the capillary. The thiophenoxide ions remove the methyl groups from internucleotide phosphotriester bonds. The capillary is then extensively washed with methanol (tubing 36) in order to completely remove the thiophenol reagent, and then evactuated with argon.

Cleavage is achieved by passing concentrated ammonium hydroxide (tubing 38) through the capillary. The ammonium hydroxide should have a residence time in the capillary sufficient to result in the cleavage of the oligo from the capillary surface. This can be achieved by passing a slug of ammonium hydroxide back and forth through the capillary at a flow rate and for a number of cycles that will achieve this result.

The eluant containing the desired oligonucleotide is treated with additional ammonium hydroxide at 60° C. for a time sufficient to remove the base protecting groups, namely N-benzoyl groups from deoxycytosines and deoxyadenosines, and N-isobutyryl groups from deoxyguanosines. The ammonium hydroxide solution is removed by vacuum drying, and finaly the last 5'-end dimethoxytrityl group is cleaved by using 80% acetic acid solution for 15 min. The reaction mixture containing the crude, unprotected deoxynucleotide is lyophilized to dryness.

The steps involving ammonium hydroxide must be undertaken with care. It is critical the concentrated ammonium hydroxide be stored properly. A small bottle of concentrated ammonium hydroxide is used for these steps and is kept tightly sealed in a freezer at −20° C. When needed, the bottle is opened quickly, an aliquot removed, and resealed immediately. After about 50% of the bottle's contents have been consumed, it is discarded. Additionally, the 60° C. step should be performed in a tightly sealed container to prevent ammonia from escaping, which will result in the base-protecting groups not being removed completely. Another potential problem is excessive exposure of the silica capillary to the concentrated ammonium hydroxide, which can lead to solubilization of the silica and contamination of the eluted sample. This can create problems when attempting to purify the oligonucleotide.

The final product is a mixture of the oligonucleotide of interest, cleaved protective groups, oligonucleotides with internal deletions, and possibly incompletely deprotected oligonucleotides. If so desired, the oligonucleotide of interest can be purified by techniques such as ethanol precipitation, size-exclusion chromatography, reverse-phase chromatography, or polyacrylamide gel electrophoresis.

Example 11

Synthesis of Peptide or Polynucleotide in Polystyrene Capillary

A 10 m section of polystyrene tubing (inner diameter of between 50 and 300 microns, available from Paradigm Optics, Inc.) is Friedel Crafts chloromethylated using chloromethyl ether in the presence of zinc chloride, in an adaptation of the method described by Feinberg and Merrifield (1974) *Tetrahedron* 30:2009. Aminomethyl groups may be introduced by Gabriel Synthesis, as described by Mitchell et al. (1976) *Tetrahedron Lett.* 3795. Hydroxymethyl groups can be attached by displacement of chloride with acetate ion followed by hydrazinolysis or hydrolysis (Erickson and Merrifield (1973) *J. Am. Chem Soc.* 95:3757, or Wang (1975) *J. Org Chem.* 40:1235).

An alternative method of chloromethylating the polymer is that described by Barron and Fritz (1983) Reactive Polymers 1:215, using concentrated hydrochloric acid and parafomaldehyde without a Lewis acid catalyst. Control of the extent of chloromethylation is possible by adjusting the concentration of reagents, the reaction temperature, and the reaction time. Following the chloromethylation step, amination is carried out by adding a large excess of 25% triethylamine in methanol or water and allowing the reaction to proceed to the desired extent.

The amino-functionalized capillary can then be used as a substrate for the synthesis of a peptide or polynucleotide as described in the foregoing examples.

While the invention has been described in connection with specific embodiments thereof, it will be understood that it is capable of further modifications and this application is intended to cover and variations, uses, or adaptations of the invention that follow, in general, the principles of the invention, including such departures from the present disclosure as come within known or customary practice within the art to which the invention pertains and as may be applied to the essential features hereinbefore set forth. Moreover, the fact that certain aspects of the invention are pointed out as preferred embodiments is not intended to in any way limit the invention to such embodiments.

What is claimed is:

1. A method of synthesizing a biopolymer on the internal surface of a capillary, comprising the steps of:
    (i) covalently attaching a first chemical entity to the internal surface of a capillary; and
    (ii) covalently attaching a second chemical entity to the first chemical entity,
    (iii) optionally repeating the attachment iteratively with the attachment of additional chemical entities, wherein the covalent attachment steps are part of a process for synthesizing the biopolymer on the internal surface of the capillary, and
wherein the capillary has an internal diameter from a lower limit of 20 µm to an upper limit of 1 mm and a length greater than 1 cm and less than 5 m.

2. The method of claim 1, wherein the capillary is tubular.

3. The method of claim 1, wherein the capillary comprises an inorganic substance selected from silica, fused silica, porous glass, aluminosilicates, borosilicates, metal oxides, or clay, or an organic substance selected from polyamide, polyether, polystyrene, polycarbonate, fluoropolymers, or mixtures thereof.

4. The method of claim 1, wherein the synthesized biopolymer is cleaved off the internal surface by passing a slug of cleavage solution through the capillary, wherein the slug of cleavage solution has a volume less than the total capillary volume.

5. The method of claim 4, wherein the synthesized biopolymer is collected in the leading edge of the slug of cleavage solution.

6. The method of claim 1, wherein the biopolymer is a polypeptide.

7. The method of claim 1, wherein the biopolymer is a polysaccharide.

8. The method of claim 1, wherein the biopolymer is a polynucleotide.

9. A method of synthesizing a biopolymer on the internal surface of a capillary, comprising the steps of:
    (i) covalently attaching a first chemical entity to the internal surface of a capillary; and
    (ii) covalently attaching a second chemical entity to the first chemical entity,
    (iii) optionally repeating the attachment iteratively with the attachment of additional chemical entities, wherein the covalent attachment steps are part of a process for synthesizing the biopolymer on the internal surface of the capillary,
    (iv) optionally removing substantially all liquid from the capillary; and
    (v) passing a slug of cleavage solution through the capillary to cleave the synthesized biopolymer off the internal surface of the capillary,
    wherein the capillary has an internal diameter from a lower limit of 20 µm to an upper limit of 1 mm and a length greater than 1 cm and less than 5 m, and
    wherein the slug of cleavage solution has a volume less than the total capillary volume.

10. The method of claim 9, wherein the capillary comprises an inorganic substance selected from silica, fused silica, porous glass, aluminosilicates, borosilicates, metal oxides, or clay, or an organic substance selected from polyamide, polyether, polystyrene, polycarbonate, fluoropolymers, or mixtures thereof.

11. The method of claim 9 wherein the capillary is tubular.

12. The method of claim 9, wherein the synthesized biopolymer is collected in the leading edge of the slug of cleavage solution.

13. The method of claim 9, wherein the total number of chemical entities is at least 40.

14. The method of claim 9, wherein step (iv) is performed and the slug of cleavage solution is passed back and forth through the channel.

15. The method of claim 9, wherein the linkage between the first chemical entity and the internal surface comprises a chemical handle.

16. The method of claim 9, wherein the first chemical entity is covalently attached to the internal surface by use of an activated functional group.

17. The method of claim 9, wherein the biopolymer is a polypeptide.

18. The method of claim 9, wherein the biopolymer is a polysaccharide.

19. The method of claim 9, wherein the biopolymer is a polynucleotide.

20. A method of synthesizing biopolymers on the internal surface of a plurality of capillaries, comprising the steps of:
   (i) covalently attaching a first chemical entity to the internal surface of each capillary; and
   (ii) covalently attaching a second chemical entity to the first chemical entity,
   (iii) optionally repeating the attachment iteratively with the attachment of additional chemical entities, wherein the covalent attachment steps are part of a process for synthesizing the biopolymers on the internal surface of the capillaries,
   (iv) optionally removing substantially all liquid from the capillaries; and
   (v) passing a slug of cleavage solution through the capillaries to cleave the synthesized biopolymer off the internal surface of the capillaries,
   wherein each capillary has an internal diameter from a lower limit of 20 $\mu$m to an upper limit of 1 mm and a length greater than 1 cm and less than 5 m, wherein each capillary is addressable and wherein the slug of cleavage solution has a volume less than the total capillary volume.

* * * * *